United States Patent [19]

Schwengers et al.

[11] 3,969,538

[45] July 13, 1976

[54] RECOVERY OF ENZYMES WITH ION EXCHANGERS

[75] Inventors: Dieter Schwengers, Dormagen; Hans Georg Schneider, Euskirchen; Ingrid Keller, Monchengladbach, all of Germany

[73] Assignee: Pfeiffer and Langen, Cologne, Germany

[22] Filed: Jan. 16, 1975

[21] Appl. No.: 541,670

[30] Foreign Application Priority Data

Jan. 17, 1974 Germany............................ 2402226
Aug. 21, 1974 Germany............................ 2439989

[52] U.S. Cl.............................. 426/491; 195/31 R; 195/31 F; 195/66 R
[51] Int. Cl........................... C07g 7/02; A23c 9/14
[58] Field of Search............. 195/66 R, 66 A, 66 B, 195/31 R, 31 F, 115; 426/491; 127/46 A

[56] References Cited
UNITED STATES PATENTS

| | | | |
|---|---|---|---|
| 3,642,580 | 2/1972 | Ghose | 195/66 R X |
| 3,649,456 | 3/1972 | Benneville et al. | 195/66 R |
| 3,720,583 | 3/1973 | Fisher | 195/115 X |

OTHER PUBLICATIONS
Methods in Enzymology, vol. 22, pp. 287–321.

*Primary Examiner*—Lionel M. Shapiro
*Attorney, Agent, or Firm*—Burgess, Dinklage & Sprung

[57] ABSTRACT

A process for separating enzymes from an aqueous solution in which they are mixed with smaller organic molecules, comprising passing the solution through an ion exchange resin, eluting the resin with water, and separating an enzyme-rich fraction before the appearance of a fraction of the eluate containing the smaller organic molecules. The solution and resin are preferably adjusted to that pH from 3 to 9 which is optimum for the catalytic action of the enzyme so the enzyme-rich fraction can thereafter directly be used for biocatalysis. The process can be used to separate lactose from milk, to separate hydrolases from the product obtained by treatment of polysaccharides, invertases from the product obtained by treatment of low saccharides, as well as of hydrolases and invertases jointly from the product obtained by treatment of polysaccharides.

18 Claims, 1 Drawing Figure

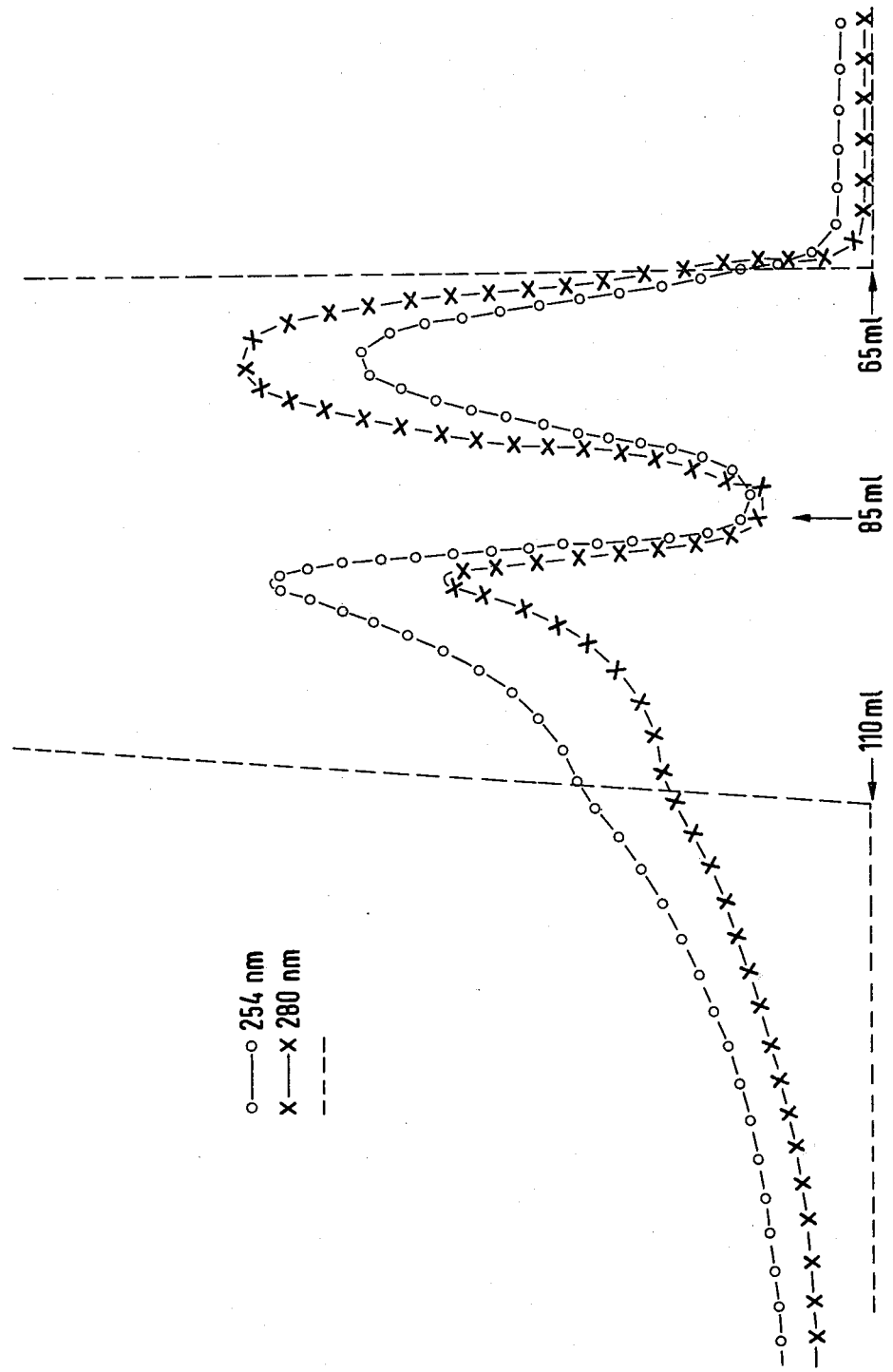

3,969,538

RECOVERY OF ENZYMES WITH ION EXCHANGERS

BACKGROUND

The invention relates to a method of extracting enzymes from aqueous solutions in which they are contained in a mixture with smaller organic molecules.

Processes for the separation of enzymes from solutions without denaturing them are known. Thus, a method is described in the technical bulletin of Pharmacia Chemicals AB of Uppsala, Sweden, entitled "Industrial Gel Filtration with the Sephamatic System", in which enzymes are separated from solutions by gel chromatography. This process, however, is very expensive. It is suitable, for example, for research laboratories, but not for the larger amounts of liquids produced in technical operations, from which enzymes must be separated. German Offenlegungsschrift No. 2,039,222 discloses a process for the separation of enzymes from liquid media by pressure filtration through a semipermeable wall. This process is also known by the name of "ultrafiltration" or "reverse osmosis". It requires a heavy investment in apparatus and operates so slowly that it is poorly suited to the separation of enzymes from relatively large amounts of solution.

THE INVENTION

The invention is addressed to the problem of simplifying the separation of enzymes from aqueous solutions in which they are contained in a mixture with smaller organic molecules, thereby enabling it to be performed economically and also on a larger, technical scale.

In the state of the art it was not possible to obtain protein substances from solutions by means of ion exchangers. Instead it was necessary to remove the protein substances contained in technical liquids before the liquids were demineralized by ion exchangers, for the purpose of preventing the exchangers from becoming clogged by the protein substances adsorbed and coagulated thereon.

It has now surprisingly been found that enzymes can be separated from smaller organic molecules by passing them through technical ion exchangers without having the protein substances become adsorbed on the ion exchangers or denatured. At the same time, the activity of the enzymes is preserved to such an extent that they can be re-used after separation.

The subject matter of the invention is a process for recovering enzymes from aqueous solutions in which they are contained in a mixture with smaller organic molecules, which is characterized by passing the solution through an ion exchange resin, eluting the resin with water, and obtaining an enzyme-rich fraction before the occurrence of the fraction of the eluate which contains the smaller organic molecules.

Suitable for the performance of the process of the invention are the known ion exchangers used on an industrial scale for the desalting of liquids, especially polystyrene sulfonate cation exchangers cross-linked with 2 to 8 wt.-% of divinyl benzene. Particularly suitable are cation exchange resins which are charged predominantly with metal ions and/or ammonium ions, and which are adjusted, like the aqueous solution to be treated, to a pH value of 3 to 9, it being a preferred measure, in the method of the invention, to adjust the aqueous solution to be treated, and the ion exchange resin as well, to the optimum pH value for the catalytic activity of the enzyme.

In a preferred embodiment, the enzyme fraction that is separated is delivered for use as a biocatalyst. Especially, the enzyme can be separated from the reaction products of its biocatalytic action and the enzyme-rich extract can be used again for this biocatalysis.

Preferably, the hydrolases active in the hydrolysis of polysaccharides to mono-, di- or oligosaccharides are extracted from solutions of the mono-, di- or oligosaccharides, and the hydrolases thus extracted are used again for the hydrolysis of polysaccharides. In like manner, invertases and isomerases can be extracted from sugar solutions and can be re-used for their specific purpose. Also embraced within the process of the invention is the joint extraction of hydrolases and isomerases followed by their re-use for the hydrolysis of polysaccharides and for the isomerization of mono- or disaccharides.

In a preferred embodiment of the process of the invention, enzyme-rich and glucose-rich fractions and enzyme-rich and fructose-rich fractions are obtained; in another embodiment, enzyme-rich, glucose-rich, glucose-and-fructose-rich and fructose-rich fractions are obtained successively from the eluate.

In still another embodiment of the invention, milk is passed through an ion exchange resin; the resin is eluted with water, and first an enzyme-rich fraction is obtained, and then a lactose-rich fraction.

The separating principle of the invention can be interpreted theoretically as follows, without restricting the invention to such interpretation:

Ion exchangers are cross-linked polymers, such as polystyrene, for example, which are shot through with fine passages of molecular size. The passages are filled with water in the operating state. Ionic groups, such as acid sulfo groups, for example, are bound to the surface of the polymer. To each ionic group correspond ions of opposite charge of "counter-ions", which are not bound to the polymeric network and are therefore replaceable. Enzymes are higher molecular substances having many ionic groups which can interact with the ionic groups of the ion exchanger. If this interaction becomes so great that a counter-ion of the exchanger is replaced, the enzyme then becomes absorbed onto the exchanger.

By the selection of suitable counter-ions on the ion exchanger, it is possible to minimize the interaction between the ionic groups of the exchanger and those of the enzyme.

If an aqueous solution containing an enzyme plus smaller organic molecules is passed through a chromatography column filled with a suitable ion exchanger, the enzyme will move with the flow of the water through the interstices between the particles of the ion exchange resin, without being affected by the latter. On account of its molecular size, however, the enzyme is denied access to the water in the fine passages within the ion exchange resin (molecular exclusion). But smaller, uncharged organic molecules diffuse, according to their size, into a portion of the passages, or even into all of the passages, within the particles of the ion exchanger, so that, in passing through the chromatography column, they travel a longer distance than the enzyme.

Salts are unable to penetrate into the fine passages, even if they are small molecules or ions, because they are blocked therefrom by the bound ionic groups of the ion exchanger due to the repulsion of the like electrical charge (ion exclusion). They are therefore eluted together with the enzymes.

The appearance of enzymes in the eluate of the columns filled with ion exchangers can be detected by continuous measurement of the ultraviolet absorption of the eluate at certain wavelengths, thereby permitting an optimum separation of fractions in the extraction of the enzymes. The measuring arrangement necessary for this purpose is often too expensive in technical columns. However, in experiments with small columns filled with polystyrene sulfonate cation exchangers, in which the eluate was passed continuously through the cell of a photometer and through a conductivity measuring cell, it has been found that, if the pH of the exchanger is suitable, the enzymes leave the column as a rule together with the salts present in or added to the solution.

The appearance of enzymes in the eluate can therefore be detected indirectly simply by measuring the electrolytic conductivity. From the curve representing the ultraviolet absorption at 254 and 280 nm, which was measured simultaneously with the conductivity, in the Figure, it can be seen that the amyloglucosidase enzyme NOVO 150 (NOVO Industrie A/S, Copenhagen, Denmark) was resolved under the conditions of the process into two ultraviolet-active components. The second component which later appeared in the column has little or no enzyme activity.

There is no advantage in separating this inactive component from the active component in performing the process of the invention, since doing so would cause more of the inactive component to form at the expense of the active component. Since the active component also restores itself from the separated inactive component to a certain extent, an equilibrium is apparently involved between an active and an inactive form of the enzyme, and these can be separated by the method of the invention.

The measurement presented in the Figure was performed under the following conditions:

Column: Diameter 1.6 cm; depth of the resin 83 cm
Resin: Polystyrene sulfonate Bayer TSW 40
Pass-through rate: 0.45 bed volume/h
Specimen volume: 1 ml The ion exchanger that can be used in accordance with the invention has passages of a fineness which increases as the degree of cross-linking increases, so that ultimately only very small molecules are still able to diffuse into them. In order to select the correct degree of cross-linking it is therefore important to know what the molecular weight is of the smaller organic molecules which are to be separated from the solution containing the enzyme. The following table gives an approximate representation of the relationship between the degree of cross-linking of the ion exchanger and the molecular weight of the separable molecules for exchangers made of polystyrene sulfonate cross-linked with divinyl benzene (DVB):

| Polystyrene sulfonate exchanger cross-linked with | Molecular weight of the separable molecules |
| --- | --- |
| 8 wt.-% DVB | 16 – 300 |
| 4 wt.-% DVB | 16 – 500 |
| 2 wt.-% DVB | 16 – 800 |

The following polystyrene sulfonate cation exchangers, for example, have been used successfully for the process of the invention:

| Name | wt.-% of divinyl benzene | Manufacturer |
| --- | --- | --- |
| Bayer TSW 40 | 4 | Bayer AG, Leverkusen |
| Zerolite 225 | 4 | Permutit, London |
| Imac C 4 A | 4 | Akzo Chemie nv, Amsterdam |
| Imac C 8 P | 8 | Akzo Chemie nv, Amsterdam |
| Imac C 12 | 9 | Akzo Chemie nv, Amsterdam |
| Amberlite IR 118 | 5 | Rohm & Haas, Philadelphia |
| Amberlite IR 120 | 8 | Rohm & Haas, Philadelphia |
| Dowex 50 W X 2 | 2 | Dow Chemical, Midland |
| Dowex 50 W X 4 | 4 | Dow Chemical, Midland |
| Dowex 50 W X 8 | 8 | Dow Chemical, Midland |

The pH value of the ion exchanger may be between 3 and 9, and the best pH value is to be determined for each enzyme so that the enzyme will suffer no loss of activity in passing through the ion exchanger. The optimum pH value can be determined as follows:

DETERMINATION OF THE OPTIMUM PH VALUE 25 milliliter specimens of an amyloglucosidase solution "NOVO 150" (amyloglucosidase of NOVO Industrie, Copenhagen) having an activity of 2416 U (units) were passed through Zerolit 225 cation exchanger previously adjusted to various pH values with citrate buffers. Elution was performed with distilled water whose pH value was adjusted to that of the exchanger. The fraction containing the enzyme was intercepted as described in Example 1 and its activity was determined in a known manner:

Column: Diameter 1.2 cm, resin depth 80 cm
Resin: Zerolit 225
Rate of flow: 0.5 bed volume/h
Temperature: 50°C
Counter-ion of the resin: Na.

| Exchanger adjusted to pH | Activity of the enzyme fraction |
| --- | --- |
| 4.0 | 1863 |
| 4.5 | 2467 |
| 5.0 | 2262 |

In like manner the following optimum pH values were determined for glucose isomerase and invertase:

| | | Counter-ions of the Resin |
| --- | --- | --- |
| Glucose isomerase | pH 6.8 | Na |
| Invertase | pH 5.0 | Na |

The amyloglucosidase tested thus suffers no loss of activity in contact with the cation exchanger adjusted to pH 4.5. This pH value is the same as that at which the enzyme optimally hydrolyzes starch to glucose.

Likewise, the optimum pH value found for glucose isomerase for the separation of the enzyme of glucose and fructose by means of ion exchange resin by the method of the invention is the same as the optimum pH value for the isomerization of glucose to fructose by this enzyme.

From this it can be concluded that the pH value at which the operation of an enzyme is optimum is also the optimum pH value for the separation of the enzyme from smaller organic molecules by the method of the invention. The optimum pH ranges for the action of some enzymes are given by H. U. Bergmeier in "Methoden der enzymatischen Analyse", 2nd ed., Verlag Chemie, Weinheim, 1970, the numbers given after the names representing the enzyme nomenclature of the IUPAC (International Union of Pure and Applied Chemistry):

a) o-Glycosyl hydrolases (3.2.1)
   Amyloglucosidase from Aspergillus niger     pH 4.8, p. 396
   β-Amylase from potatoes     pH 4.8, p. 395
   Invertase     pH 4.7–4.9, p. 871
   Cellulase from Trichoderma viride     pH 4.5, p. 1101
b) Sugar isomerases (5.3.1)
   Glucose isomerase from Lactobacillus plantarum     pH 8.2*, p. 1355

*It is not practical to operate at this pH because the sugars decompose in the alkaline region.

Since the ion exchanger is adjusted to a certain pH value, a certain proportion of the counter-ions of the ion exchanger must consist of hydrogen or hydroxyl ions. The rest of the counter-ions, if cation exchangers are used, are metal and ammonium ions, preferably univalent and bivalent metal ions such as, for example, $Na^+$, $K^+$, $Mg^{2+}$ and $Ca^{2+}$, and, if anion exchangers are used, the anions of mineral acids and hydroxy acids of metals, such as for example chloride, sulfate, hydrogen sulfite, molybdate and borate.

The nature of the counter-ions will, for practical reasons, be the same, insofar as possible, as those which are already present in the solution from which the enzyme is to be separated from smaller organic molecules by the method of the invention. This is advantageous especially when the enzyme-containing fraction which also contains the salts of the enzyme-containing solution is to be reused as a biocatalyst, for in that case the enzyme-containing fraction can be mixed directly with the substrate, without having to replace the salts necessary for the action of the enzyme, such as for example cobalt salts and magnesium salts for glucose isomerase.

The temperature for the performance of the process of the application depends upon the thermal stability of the enzyme. Preferably the process is performed at temperatures between about 20° and 80°C.

The flow-through rate for the elution with water can be very high. Rates exceeding 1 bed volume per hour (BV/h) are possible depending on the viscosity of the solutions. However, it is preferable to use a rate ranging from about 0.2 to 1.0 BV/h, especially from about 0.4 to 0.9 BV/h.

The process of the application is generally applicable to the separation of enzymes from aqueous solutions. It is especially suitable for the separation of enzymes from starch hydrolysis syrups and glucose isomerization syrups, from culture broths, and from other such solutions in which enzymes are used as catalysts. Most industrial processes using enzymes as biocatalysts are batch processes in which the expensive enzymes are destroyed after the reaction has ended, after a single use, for lack of a suitable process for their recovery. For reasons of cost, therefore, low proportions of enzymes are used, resulting in long reaction times. For example, in the technical preparation of glucose from liquefied starch with amyloglucosidase as biocatalyst, the hydrolysis time amounts to 48 to 72 hours.

The process of the invention for the recovery of enzymes, however, makes it possible to use substantially larger proportions of enzymes, since the enzymes are recovered and re-used, so that the uneconomically long reaction times can be greatly reduced. Moreover, the enzyme proportion can be made so high that continuous processes can be used instead of batch processes.

For example, 1 to 3 wt.-% of amyloglucosidase can be added to a filtered starch solution previously hydrolyzed with acid or alpha amylase, the pH of the solution can be adjusted to a value between 4.0 and 7.0, and the solution can be pumped through a circulation tube at a temperature between 50° and 60°C in 1 to 6 hours. The time of stay in the circulation tube is such that when the starch solution hydrolyzed to glucose and oligosaccharides leaves the tube it will have a saccharification (dextrose equivalent) of more than 80 DE. The glucose-containing solution emerging from the circulation tube is delivered to a system of several columns packed with cation exchange resins. The ion exchange resin is buffered to pH 4.5 to 5.0, alkali and/or alkaline earth ions serving as the counter-ion for the sulfo groups of the resin. Each resin column is fed a batch volume of 5 to 35% of the resin volume. After the glucose-containing solution has seeped into the resin bed the latter is eluted with water.

The run-off from each column is advantageously divided into several fractions. The first salt fractions leaving the columns contain the amyloglucosidase and a portion of the oligosaccharides. The next fractions contain the glucose and a portion of the salts plus oligosaccharides. The third fraction consists of pure glucose. Since this glucosic fraction as a rule contains only a small amount of dry substance, it can advantageously be reserved and, after the batch volume has seeped into the resin bed, it can be fed back into the column before the column is eluted with water. This recycling method increases the dry substance content of the principal fraction thereby avoiding the necessity of concentrating very dilute sugar solutions.

The first fraction, which contains the amyloglucosidase, can be mixed with previously hydrolyzed starch solution and vacuum-concentrated down to a dry substance content of 30° to 40° Brix. Then the solution is fed into the circulation tube, and then the process is repeated. It is also possible to completely desalt the pre-hydrolyzed starch solution with ion exchangers. The desalted solution is concentrated to a dry substance content of approximately 70° Brix and diluted to a solids content of 30° to 40° Brix with the first fraction from the column, which contains the amyloglucosidase. This solution is then passed through the circulation tube.

The above-described complete desalting of the prehydrolyzed starch solution is especially advantageous if immediately after the hydrolysis of the starch to glucose a portion of the glucose is to be isomerized to fructose with glucose-converting enzymes. The principal fractions from the columns are concentrated by evaporation to a solids content of about 40° to 50° Brix for this purpose, and are reacted directly with the enzyme, glucoseisomerase, in a known manner. Since the glucose solutions used contain virtually no amino acids and protein substances, substantially less coloration is produced by the conversion of the glucose to fructose than in the known process.

By the method of the invention it is also possible to separate free glucoseisomerase from solutions containing glucose and fructose, and to re-use it. For this purpose it is, of course, necessary to use glucoseisomerase-containing solutions in which the enzyme is dissolved out of the cells, since only the dissolved portion of the enzyme can be recovered by the method of the invention, not the portion that adheres to the cells.

Lastly, the enzyme glucoseisomerase can be separated from aqueous solutions by the method of the invention, simultaneously with the enzyme amyloglucosidase, a hydrolase. This is the case, for example, when these two enzymes are employed such that, first the amyloglucosidase hydrolyzes prehydrolyzed starch to glucose, and then the glucoseisomerase converts part of the glucose to fructose. The amyloglucosidase and glucoseisomerase can also be made to act upon prehydrolyzed starch, and this leads to glucose syrups containing fructose.

Preferably, for the recovery of an enzyme fraction that is rich in glucoseisomerase, the starting substance is an aqueous solution containing essentially fructose and glucose; the maintenance of a pH ranging between 6.8 and 7.2 leads to especially good separation, inasmuch as the conversion of fructose and glucose to undesired products in the more alkaline range is thus virtually entirely excluded. It is advantageous in this case that polyvalent cations, such as for example calcium, magnesium or cobalt ions, do not interfere with the separation of glucoseisomerase in the stated pH range. It is especially advantageous to use a cation exchange resin which is charged with calcium ions. A resin pre-treated in this manner makes it possible to obtain a glucose fraction, an isomerase syrup fraction and a fructose fraction after the enzyme fraction. Accordingly, not only is an enzyme-rich fraction produced, but at the same time the advantageous separation of fructose-rich and glucose-rich fractions becomes possible, which can be processed at little cost to the pure substances, or which, after concentration of the solutions if desired, can be used directly for a variety of applications. The isomerase syrup fraction, which in addition to glucose contains fructose formed therefrom by isomerization, is subjected to the usual refining and separating processes.

Furthermore, enzymes are valuable components of foods. For example, cow's milk, the most important food for infants, contains more than 19 enzymes (K. M. Shahani et al., "Enzymes in Bovine Milk: A Review" in Journal of Dairy Science Vol. 56, 1973, pp. 531–543). The separation of the enzymes and other milk components from the lactose is of great importance, since many people are unable to tolerate normal cow's milk. This intolerance is attributed to the lactose contained in milk, since the typical symptoms, such as stomach upset and diarrhea, occur only in people who suffer an intestinal insufficiency or lack of the enzyme β-galactosidase which hydrolyzes lactose. By the process of the invention the undesired lactose is largely removed, and a high quality dietetic milk is obtained which contans the valuable enzymes as well as all of the beneficial components, i.e., milk protein, minerals, butterfat, hormones and vitamins.

The method of the invention also makes possible the extraction of enzymes by means of which racemic mixtures of substances can be separated into their optically active d and l forms. Examples are the production of L-amino acids from synthetic D,L-mixtures by specific hydrolysis of one of the two forms of their D,L-N-acylamino acid derivatives by means of aminoacylases (3.5.1.14 in the IUPAC nomenclature) or the production of l-menthol, the principal component of natural peppermint oil, by the specific ester cleavage of one of the two forms of d,l-carboxylmenthol ester mixture by means of carboxyester-hydrolases (3.1.1 in the IUPAC nomenclature).

EXAMPLES

The invention will be explained hereinafter with the aid of examples.

EXAMPLE 1

Recovery of amyloglucosidase and its re-use as a biocatalyst.

40 kilograms of corn meal were suspended in 100 kg of water at 60°C. After the addition of 112 g of $CaCl_2 \cdot 2H_2O$ the pH of the suspension was adjusted with soda to 6.5; 250 ml of alpha amylase was added, the temperature was raised to 85°C, and the suspension was stirred for 3 hours at this temperature. Then, to inactivate the alpha amylase, the temperature was increased to 100°C for 15 minutes. After cooling to 70°C, the pH was adjusted with hydrochloric acid to 4.5 and the suspension was filtered with a filter press. The dextrose equivalent of the clear filtered dextrin solution was 24.5, the solids content 26.6° Brix. This solution served as the starting solution for the experiments that follow.

To 1644 g (1.5 l) of the dextrin solution of pH 4.5, 15 ml of NOVO 150 amyloglucosidase was added and the temperature was maintained for 4 h at 55° to 60°C. The DE of the resulting glucose solution then was 94.1.

The glucose solution was delivered to a resin column which had previously been prepared in the following manner: The resin was first brought into the Ca form with $CaCl_2$ solution and then rinsed with dextrin solution until the solution flowing from the column had the same pH value of 4.5 and the same salt composition as the solution going into the column.

The polystyrene sulfonate resin, Bayer TSW 40, was then charged with calcium, sodium and potassium ions in a molar ratio of 7 : 1.8 : 1. The depth of resin was 2 meters, and the utilized resin volume was 10 liters.

After the glucose solution had been allowed to seep in, the column was eluted with distilled water of pH 4.5 at a rate of 0.5 bed volume per hour. The eluate was divided into an enzyme fraction and a glucose fraction. The enzyme fraction, which contains salts and oligosaccharides in addition to the enzyme, leaves the column approximately between liters 4 to 6.3 from the beginning of the input of the enzymatic glucose solution. The glucose fraction extended from liters 6.3 to 10.5.

The enzyme fraction was again reacted with 1644 g (1.5 l) of the dextrin solution. During the reaction the volume of the reaction solution was concentrated in vacuo to 1.5 l. The glucose solution obtained was again put through the resin column for recovery of the amyloglucosidase. In all, the same enzyme was used ten times for the recovery of glucose solution from the dextrin solution. The following tables gives information on the DE levels of the glucose solutions delivered in each case to the resin column, and the DE levels of the glucose fractions. The specimen number indicates the number of the cycle in which the same enzyme was used. Specimen No. 2, for example, indicates that the enzyme has for the second time saccharified 1644 g of the dextrin solution from 26.6° Brix and a DE of 24.5 to the stated DE level, and that the enzyme has been recovered one time by the method of the invention:

| Specimen No. | DE Level of the glucose solution | DE Level of the glucose fraction | Reaction time (h) |
|---|---|---|---|
| 1 | 94.1 | 99.5 | 4 |
| 2 | 93.8 | 98.0 | 6 |
| 3 | 95.2 | 98.4 | 6 |
| 4 | 92.3 | 95.9 | 6 |
| 5 | 89.8 | 97.1 | 6 |
| 6 | 83.5 | 97.0 | 6 |
| 7 | 83 | 98.1 | 6 |
| 8 | 88.2 | 95.3 | 12 |
| 9 | 84 | 96.6 | 12 |
| 10 | 78.4 | 95 | 15 |

The table indicates that the enzyme suffers a certain loss of activity as the number of cycles increases. As experiments have shown, this loss of activity is also based on the inhibition of the enzyme by the increasing concentration of salts and oligosaccharides which are not hydrolyzed to glucose by the amyloglucosidase. The salt content, for example, expressed in meq (milliequivalents) of acid increased in Specimen 1 from 82 meq of acid to 167.6 meq in Specimen 8.

It may therefore be advisable to subject the enzyme fraction to a purifying process after a certain number of cycles. In the case of amyloglucosidase, this can be effected advantageously by precipitating the enzyme with methanol or isopropanol.

EXAMPLE 2

Separation of milk enzymes and preparation of a low-lactose dietetic milk

Bayer TSW 40 polystyrene sulfonate resin was transformed to the sodium form with sodium chloride solution of pH 7 and adjusted to a pH of 7. The depth of the resin was 2.9 m, and the utilized resin volume was 14 l. At a column temperature of 20°C the resin colum was first rinsed with 1 bed volume (BV) of milk (rate of flow 0.5 BV/h) for the purpose of adjusting the resin to a cation composition of the type that is in the milk. The resin is then washed free of milk with distilled water. Two liters of milk whose solids contained 45.1% lactose and 28.8% protein were fed into the resin column thus prepared and then distilled water was put in. The eluate was divided into an enzyme-rich milk protein fraction and a lactose-rich fraction. The enzyme-rich milk protein fraction left the column in the 4.9 to 7.3 liter range, counting from the beginning of the input of the milk. Lactose constituted only 6.6% of the solids of this fraction. The lactose-rich fraction extended from 7.3 to 10.5 liters.

The enzyme-rich milk protein fraction of reduced lactose content was then concentrated to the normal solids content of milk (approx. 10.2%). The dietetic milk could not be distinguished visually from normal milk. Its taste was neutral. The "sweetness" which it lacked in comparison to normal milk was easily recovered by the addition of small amounts of tolerable sugars such as saccharose, fructose and/or glucose.

EXAMPLE 3

Recovery of amyloglucosidase and glucoseisomerase and their re-use as biocatalysts To 150 g of the dextrin solution of Example 1, 0.1 ml of NOVO 150 amyloglucosidase, the aqueous extract of 0.5 g of glucoseisomerase, 0.33 g of $MgSO_4 \cdot 7 H_2O$ and 0.33 g of $CoCl_2 \cdot 6 H_2O$ were added. The pH of the solution was 6 to 6.2 and was automatically readjusted during the reaction, and the temperature was maintained at 55° to 60°C. After 24 h a DE of 84 had been reached. The percentage of fructose in the reducing sugars amounted to 28%.

By the method of the invention, the amyloglucosidase mixed with the glucoseisomerase was recovered. Experimental data:
Column: Diameter 1.6 cm, resin depth 85 cm.
Resin: Imacti C-4-A
Counter-ions: Sodium
pH value: 6.4
Temperature: 40°C Dextrin solution was again reacted with the aid of the recovered enzyme mixture. After 24 hours the DE was 75 and the percentage of fructose in the reducing sugars was 20.8%.

EXAMPLE 4

Recovery of invertase and its re-use as a biocatalyst.

A 50% aqueous saccharose solution in the form of pure saccharose, containing 0.1% invertase (Merck Prod. No. 7684), was inverted at pH 4.5 and 55°C. 16 hours later the hydrolysis of the saccharose to glucose and fructose had ended and the invertase was recovered under the following conditions. Experimental conditions:
Column: Diameter 8 cm, Resin depth 290 cm
Resin: Bayer TSW 40 polystyrene sulfonate
Counter-ions: $Na^+$
pH: 5.0
Temperature: 40°C
Rate of flow: 0.037 cm/sec (0.45 bed volumes per h)

Saccharose was again inverted with the enzyme fraction. The saccharose was 92% hydrolyzed in 16 hours.

EXAMPLE 5

Recovery of glucoseisomerase and its re-use as a biocatalyst.

In order to isomerize glucose enzymatically to fructose, 5 kg of an aqueous solution containing 2200 g of glucosemonohydrate, 1 g of cobalt(II) chloride hexahydrate and 8 g of glucoseisomerase enzyme (Miles Kali Chemie, sample containing 3000 TGIU/g) was stirred at 70°C. The solution had been prepared with tap water whose $Ca^{++}$ ions had been replaced with $Mg^{++}$ ions by means of ion exchangers. The pH of the solution was 7.0 and was readjusted automatically with soda lye during the reaction.

After 18 hours the percentage of fructose in the solids was 40.2 wt.-%. The solution was then cooled to room temperature and filtered, and fed to a separating column 8 cm in diameter filled with Bayer TSW 40 polystyrene sulfonate resin to a depth of 290 cm, for the recovery of the enzyme glucoseisomerase. At a column temperature of 25°C, the column was eluted at the rate of 0.04 cm/sec (0.5 bed volume per hour) with water. The eluate from the column was divided into the following fractions:
First runnings (water) from 0.0 to 5.0 liters
Enzyme fraction from 5.0 to 10.0 liters
Glucose fraction from 10.0 to 11.0 liters (90.6% Glu, 9.4% Fru)
Isomerase syrup frac. from 11.0 to 19.0 liters (56.1% Glu, 43.9% Fru)
Fructose fraction from 19.0 to 21.5 liters (8.2 % Glu, 91.8% Fru)

To replace $Ca^{++}$ ions with $Mg^{++}$ ions, the enzyme fraction was passed through a cation exchanger charged with $Mg^{++}$ ions. For the further conversion of glucose to fructose, 2200 g of glucose monohydrate and 1 g of cobalt(II) chloride hexahydrate were dissolved in the exchanged enzyme fraction, the solution was concentrated in vacuo to 5 kg, and was stirred as before at 70°C. After 30 hours the solution contained 35 wt.-% fructose.

For the recovery of the glucoseisomerase enzyme, the solution was again passed through the separating column and the eluate was divided into fractions as before. The enzyme fraction thus obtained was used a third time for the isomerization of 2200 g of glucose monohydrate. A total of 2104 g of fructose was obtained from 6000 g of glucose (6600 g of glucose monohydrate).

It will be appreciated that the instant specification and Examples are set forth by way of illustration and not limitation and that various modifications and changes may be made without departing from the spirit and scope of the present invention.

What is claimed is:

1. A process for separating enzymes from an aqueous solution in which they are mixed with smaller organic molecules, comprising passing the solution through an ion exchange resin, eluting the resin with water, and separating an enzyme-rich fraction before the appearance of a fraction of the eluate containing the samller organic molecules.

2. The process of claim 1, wherein the ion exchange resin is a cation exchange resin charged with at least one of metal ions and ammonium ions.

3. The process of claim 1, wherein the aqueous solution to be treated and the ion exchange resin are adjusted to a pH value of about 3 to 9 prior to passage of the solution through the resin.

4. The process of claim 3, wherein the aqueous solution to be treated and the ion exchange resin are adjusted to that pH value which is optimum for the catalytic action of the enzyme.

5. The process of claim 4, including the further step of contacting the extracted enzyme fraction with material to be catalyzed thereby.

6. The process of claim 5, wherein the catalyzed product of the further step is treated to remove an enzyme-rich fraction which is re-cycled for further catalysis.

7. The process of claim 1, wherein the aqueous solution conains mono-, di- or oligosaccharides in admixture with hydrolases which are active in the hydrolysis of polysaccharides to such mono-, di- and oligosaccharides.

8. The process of claim 7, including the further step of contacting the extracted hydrolases with an aqueous medium containing polysaccharides.

9. The process of claim 1, wherein the aqueous solution contains invertase and mono-, di- and trisaccharides.

10. The process of claim 1, wherein the aqueous solution contains invertase and monosaccharides, the method including the further step of contacting the invertase fraction with aqueous disaccharides to form further monosaccharide-containing aqueous solution.

11. The process of claim 1, wherein the aqueous solution contains at least one of mono-, di- and oligosaccharides in admixture with isomerases active in the isomerization of mono- and di-saccharides.

12. The process of claim 11, including the further step of contacting the extracted isomerases with an aqueous medium containing mono- and di-saccharides.

13. The process of claim 12, wherein the hydrolases and isomerases are jointly extracted, the method including the further step of contacting the joint enzyme fraction with aqueous polysaccharide to effect hydrolysis of the polysaccharide to mono- and di-saccharides and isomerization of such mono- and di-saccharides.

14. The process of claim 12, wherein the eluate is divided into an enzyme-rich fraction and a glucose-rich fraction.

15. The process of claim 12, wherein the eluate is divided into an enzyme-rich fraction and a fructose-rich fraction.

16. The process of claim 12, wherein the eluate is successively divided into an enzyme-rich fraction, a glucose-rich fraction, a glucose-and-fructose-rich fraction and fructose-rich fraction.

17. The process of claim 3, wherein the aqueous solution is milk and the eluate is successively divided into an enzyme-rich fraction and then a lactose-fraction.

18. The process of claim 1, including the steps of measuring the electrolytic conductivity of the eluate, commencing collection of the enzyme-rich fraction when the conductivity rises and discontinuing collection of such fraction when the conductivity falls.

* * * * *